US00PP11705P

United States Patent [19]

Bradford et al.

[11] Patent Number: Plant 11,705

[45] Date of Patent: Dec. 19, 2000

[54] NECTARINE TREE NAMED 'CANDY GOLD'

[76] Inventors: Lowell Glen Bradford, 12439 E. Savana Rd.; Norman G. Bradford, 11875 E. Savana Rd., both of Le Grand, Calif. 95333

[21] Appl. No.: 09/229,635

[22] Filed: Jan. 13, 1999

[51] Int. Cl.[7] ..... A01H 5/00

[52] U.S. Cl. ..... Plt./190

[58] Field of Search ..... Plt./190

[56] References Cited

U.S. PATENT DOCUMENTS

P.P. 7,193 3/1990 Bradford ..... Plt./190

*Primary Examiner*—Howard J. Locker
*Assistant Examiner*—Wendy A Baker

[57] ABSTRACT

The present invention relates to a nectarine tree, *Prunus persica*, and more particularly to a new and distinct variety broadly characterized by a large size, vigorous, self-fertile, productive and regular bearing tree. The fruit matures under the ecological conditions described approximately the last week in July, with first picking on Jul. 25, 1998. The fruit is uniformly medium in size, subacidic and sweet in flavor, globose in shape, clingstone in type, very firm and crisp in texture, and full red in skin color. The variety was a first generation cross using 'Red Glen' (U.S. Plant Pat. No. 7,193) nectarine as the seed parent and an unnamed white flesh nectarine seedling as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'Candy Gold'. The present variety was developed by us in 1992 in a cultivated area of our experimental orchard at Bradford Farms near Le Grand, Calif. in a Merced County (San Joaquin Valley). It was a first generation cross using 'Red Glen' (U.S. Plant Pat. No. 7,193) nectarine as the seed parent and an unnamed white flesh nectarine seedling as the selected pollen parent. Subsequent to origination of the present variety of nectarine tree, we asexually reproduced it by budding and grafting on Nemaguard (unpatented) rootstock, in the experimental orchard described above, and such reproduction of plant and fruit characteristics were true to the original plant in all respects.

The present variety is most similar to its seed parent, the 'Red Glen', by producing yellow flesh clingstone nectarines that are full red in skin color, very firm in texture, and that ripen the last week in July, but is distinguished therefrom and an improvement thereon by having a showy instead of nonshowy blossom, by having a bitter instead of sweet kernel, and by producing fruit that is subacid instead of acid in flavor, that is much sweeter, and that is somewhat larger in size.

BRIEF DESCRIPTION OF THE DRAWING

The accompanying photograph exhibits four whole fruits positioned to display the characteristics of the skin color and form, a sectioned fruit sliced transverse to the suture plane to reveal the flesh and stone, and representative leaves. The colors illustrated are as close as is reasonably possible to attain in a photographic illustration of this character, however the color designations set forth in the specification should be considered to be controlling.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard shipping ripe on Aug. 2, 1998. All major color code designations are by reference to the Inter-Society Color Council, National Bureau of Standards. Common color names are also used occasionally.

TREE

Size: Large, reaching a height of 12' [3.66 meters] by the 5th year of growth, including typical dormant pruning.

Vigor: Vigorous, responding typically to irrigation and fertilization. The plant should be grown on a standard commercial rootstock for production purposes.

Growth: Upright and dense.

Form: Vase formed.

Hardiness: Hardy with respect to typical central California winters.

Production: Productive, thinning usually necessary.

Fertility: Self-fertile.

Bearing: Regular bearer, with no alternate bearing observed.

Trunk:

- *Size.*—Medium, reaching a maximum diameter of 5.5" [140 mm.] after 5 years of growth.
- *Texture.*—Medium to somewhat shaggy.
- *Bark color.*—Grayish yellowish brown [80. gy.yBr].
- *Lenticels.*—Numerous. Color: Dark grayish brown [62. d.gy.Br]. Typical Size: 1/8" to 3/8" [3.2–9.5 mm.].

Branches:

- *Size.*—Medium, typical of the species.
- *Texture.*—Smooth on 1st year wood, increasing roughness with age.
- *Color.*—1st Year Wood Topside: Moderate pink [5. mPk]. 1st Year Wood Underside: Brilliant yellow green [116. brill.YG]. Older Wood: Moderate brown [58. m.Br].
- *Lenticels.*—Numerous, small. Color: Grayish brown [61. gy.Br]. Average Size: 1/16" [1.6 mm.].

Leaves:

- *Size.*—Large. Average Length: 6" [152.4 mm.]. Average Width: 1 5/8" [41.3 mm.].
- *Thickness.*—Medium.
- *Form.*—Elliptical.
- *Apex.*—Acute to acuminate.

*Base.*—Acute.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: 3/8" [9.5 mm.]. Average Thickness: 1/16" [1.6 mm.]. Color: Brilliant yellow green [116. brill.YG].
*Stipules.*—2 per leaf bud, up to 6 at the growing tip. Average Length: 3/8" [9.5 mm.].
*Glands.*—Numbers: Usually 2 per leaf, occasionally 3 or 4. Position: Oppositely positioned on petiole and base of blade. Size: Small. Form: Globose. Color: Deep reddish brown [41. deep rBr].

Flower buds:
*Hardiness.*—Hardy with respect to central California winters.
*Diameter.*—Typically 3/8" [9.5 mm.] 1 week before bloom.
*Length.*—Typically 3/4" [19.1 mm.] 1 week before bloom.
*Form.*—Free.
*Surface.*—Pubescent.

Flowers:
*Blooming period.*—Medium as compared with other varieties.
*Onset of bloom.*—One percent on Feb. 27, 1998.
*Duration of bloom.*—One to two weeks, dependent on ambient temperature.
*Type.*—Showy.
*Average diameter.*—1 7/8" [47.6 mm.].
*Color.*—Pale purplish pink [252. p.pPk].
*Fragrance.*—None to slight.

FRUIT

Maturity when described: Hard shipping ripe, Aug. 2, 1998.
Date of first picking: Jul. 25, 1998.
Date of last picking: Aug. 9, 1998.
Size: Uniform, medium.
*Average diameter axially.*—2 1/2" [63.5 mm.].
*Average transversely in suture plane.*—2 5/8" [66.7 mm.].
*Typical weight.*—5.85 ounces [166 grams].
Form: Globose, uniform, symmetrical to slightly unsymmetrical.
*Longitudinal section form.*—Round to slightly oblong.
*Transverse section through diameter.*—Round.
Suture: A sharp groove very near the stem, an inconspicuous line along the lateral surface, and a shallow groove toward the apex with a slight depression beyond the pistil point.
Ventral surface: Rounded, lipped toward the apex.
Lips: Mostly equal.
Cavity: Flaring, slightly elongated in the suture plane, suture showing on one side, stem markings typical.
*Depth.*—1/2" [12.7 mm.].
*Breadth.*—3/4" [19.1 mm.].
Base: Rounded to slightly truncate.
Apex: Rounded.
Pistil point: Oblique, negligible in length, indented within the suture.
Stem: Medium.
*Average length.*—3/8" [9.5 mm.].
*Average width.*—3/16" [4.8 mm.].

Skin:
*Thickness.*—Medium.
*Texture.*—Medium.
*Tenacity.*—Tenacious to flesh.
*Tendency to crack.*—None observed.
*Color.*—Very dark red [17. v.d.R] over a strong red [12. s.R] background with very slight light orange yellow [70. l.OY] freckling on the sides and toward the apex.

Flesh:
*Color.*—Brilliant orange yellow [67. brill.OY] with dark red [16. d.R] streaking toward the stone.
*Surface of pit cavity.*—Dark red [16. d.R] fibers breaking when twisted away from the stone.
*Amygdalin.*—Scarce.
*Juice.*—Abundant, rich.
*Texture.*—Firm, crisp.
*Fibers.*—Abundant, fine.
*Ripens.*—Slightly earlier at the apex.
*Flavor.*—Subacidic and sweet, typically 16 to 18 brix.
*Aroma.*—Slight.
*Eating quality.*—Very good.

STONE

Type: Clingstone.
Form: Oval.
Base: Straight.
Apex: Acute.
Hilum: Narrow.
Sides: Equal.
Surface: Irregularly furrowed toward the apex, pitted near the base.
Ridges: Jagged toward the base.
Color: Dark yellowish brown [78. d.yBr] when first removed from fruit.
Pit wall: 1/4" [6.4 mm.] thick.
Average width: Approximately 15/16".
Average length: Approximately 1 5/16".
Tendency to split: Slight in wet season.
Kernel:
*Form.*—Oval.
*Taste.*—Bitter.
*Viable.*—Yes.
*Average width.*—7/16" [11.1 mm.].
*Average length.*—13/16" [20.6 mm.].
*Skin color.*—Vivid orange yellow [66. v.OY] with grayish brown [61. gy.Br] veins when first removed from stone.
*Pellicle color.*—Grayish brown [61. gy.Br].
*Amygdalin.*—Abundant.

USE

Market: Fresh and long distance shipping.
Keeping quality: Fruit quality observed to remain in good condition in excess of 17 days in cold room at 36° Fahrenheit [2° Celsius].
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed parent, the 'Red Glen' (U.S. Plant Pat. No. 7,193), by producing yellow flesh clingstone nectarines that are full red in skin color, very firm in texture, and that ripen the last week in July, but is distinguished therefrom and an improvement thereon by having a showy instead of nonshowy blossom, by having a bitter instead of sweet kernel, and by producing fruit that is subacid instead of acid in flavor, that is much sweeter, and that is somewhat larger in size.

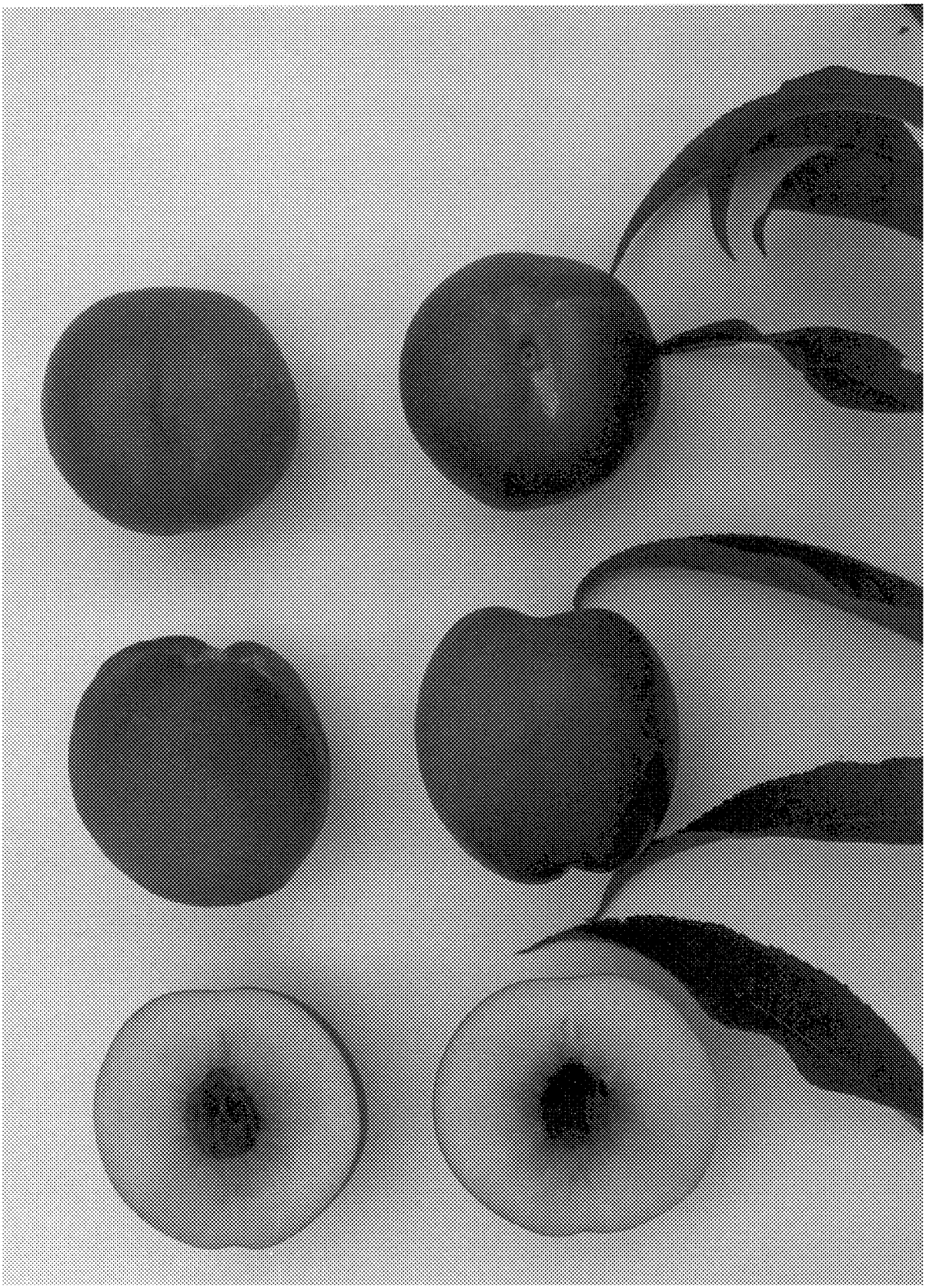

* * * * *